United States Patent [19]

Zaffaroni et al.

[11] 4,352,791

[45] Oct. 5, 1982

[54] POTASSIUM REPLACEMENT THERAPY

[75] Inventors: Alejandro Zaffaroni, Atherton; John Fara, Saratoga, both of Calif.

[73] Assignee: ALZA Corporation, Palo Alto, Calif.

[21] Appl. No.: 257,540

[22] Filed: Apr. 27, 1981

[51] Int. Cl.$^3$ ..................... A61K 31/60; A61K 33/14
[52] U.S. Cl. .................................. 424/153; 424/230
[58] Field of Search .............................. 424/153, 230

[56] References Cited

U.S. PATENT DOCUMENTS 3,337,404  8/1967  Polli et al. ........................... 424/153
3,676,553  7/1972  Reynolds ............................. 424/153
3,822,344  7/1974  Corker et al. ....................... 424/319

OTHER PUBLICATIONS

Merck Index (1976), 9th Ed., p. 1080.

Primary Examiner—Stanley J. Friedman
Attorney, Agent, or Firm—Paul L. Sabatine; Edward L. Mandell

[57] ABSTRACT

A composition is disclosed comprising potassium chloride and a therapeutically acceptable salicylate salt or salicylic acid. The composition is useful for potassium therapy.

19 Claims, No Drawings

POTASSIUM REPLACEMENT THERAPY

FIELD OF THE INVENTION

This invention pertains to a composition comprising potassium chloride and salicylic acid or a salicylate salt for potassium replacement therapy.

BACKGROUND OF THE INVENTION

The animal body, including humans, needs potassium for maintaining its health. Potassium is of fundamental importance in the ionic exchange of cellular metabolism, and it is the predominating cation of intracellular fluids and erythrocytes. Potassium ions participate in a number of essential physiological processes, including the maintenance of intracellular tonicity, the transmission of nerve impulses, the contraction of muscles, and the maintenance of normal renal function.

A deficit of potassium or potassium depletion, also known as hypokalemia, can be induced in the body in a variety of ways. A deficit of potassium may occur when the dietary intake is less than the daily animal requirement needed to substantially avoid a deficiency state. Potassium depletion also may occur through potassium losses from the gastrointestinal tract such as by vomiting or diarrhea, by losses through the genitourinary system, the latter often as a consequence of the use of diuretic drugs and minerals-corticoids, and in diseases characterized by an increased secretion of glucocorticoids.

The common treatment of a potassium depleted state generally consists in orally administering potassium chloride. While this treatment may supply the needed treatment, there are reports of gastro-intestinal ulceration associated with the use of this particular compound. The pharmacology of potassium therapy is presented in *The Pharmacological Basis of Therapeutics*, 4th Ed., by Goodman and Gilman, pages 794 to 801, 1970 published by the MacMillian Co., and in *Pharmacology In Medicine*, by Drill, pages 702 to 704, 1965, published by McGraw-Hill, Inc.

DESCRIPTION OF THE INVENTION

Accordingly, in view of the above discussion, it is an immediate object of this invention to provide an improvement in potassium replacement therapy for use in the management and prevention of a potassium deficiency in animals, including mammals and humans.

Another object of the invention is to provide a composition comprising potassium chloride and salicylic acid or a salicylate salt for satisfying the daily requirements.

Another object of the invention is to provide an improvement in potassium replacement therapy, which method consists essentially in administering orally a therapeutically effective amount of potassium chloride for treating a potassium deficit, and concomitantly administering salicylic acid or a salicylate salt for lessening the incidence of ulceration associated with this therapy.

The potassium chloride can be administered to an animal for the management of potassium depletion in a pharmaceutical composition comprising potassium chloride and salicylic acid or a salicylate salt. The salicylate salts useful for the present purpose are the pharmaceutically acceptable salts of salicylic acid such as potassium salicylate, sodium salicylate, and the like. The composition can be administered in dosage forms such as compressed tablet, an enteric coated tablet, a tablet coated with a layer sufficiently permeable to permit slow diffusion, a capsule, the drug dispersed in a polymer, embedded in a non-digestable and non-eroding porous carrier with drug released through the pores, drug dispersed in a wax matrix, as sustained release pellets, delivered from a drug delivery system such as an osmotic device, and the like.

The amount of potassium chloride in a drug dosage form is a therapeutically effective amount of potassium chloride for managing the potassium requirement of an animal, including a therapeutically effective amount for treating potassium depletion and for reversing a potassium deficit. The amount of potassium chloride in a dosage form generally is about 15 milligrams to 1200 milligrams, and more preferably from 15 milligrams to 600 milligrams. The amount of salicylic acid or a salicylate salt in a dosage form is generally an effective amount for lessening and or avoiding potassium chloride associated side-effects such as nausea, vomiting, diarrhea, and gastric and intestinal ulceration. Generally the amount of salicylic acid or a salicylate salt in the dosage form, or administered simultaneously with the potassium chloride is about 0.5 milligrams to 5 milligrams for each 5 milligrams to 20 milligrams of potassium chloride, and in a more presently preferred amount of about 1 milligram of salicylic acid or a salicylate salt for each 15 milligrams of potassium chloride. The therapeutically effective amount administered for satisfying the body's need for the potassium cationic electrolyte can be achieved by administering orally the dose formulation from 1 to 10 times a day. Many patients in need of potassium can be clinically managed by a therapeutic regimen comprising a diet of foods high in potassium such as apricots, avocados, bananas, cherries, dried fruits, tomatoes, and the like supplement with the dosage form for administering additional potassium.

The dosage formulations are manufactured by standard procedures and these are represented by the following examples. A compressed tablet comprising 300 milligrams of potassium chloride and 20 milligrams of salicylic acid or a salicylate salt is prepared by blending the two salts, and then adding thereto 20 milligrams of polyvinylpyrrolidone binder and 2 milligrams of Carbnwax ® lubricant to form a homogenous composition. A tablet is formed in a tablet machine by exerting a pressure of 1½ tons on the composition in a die cavity shaped like a tablet. An enteric coated tablet is represented by a tablet comprising 300 milligrams of potassium chloride, 20 milligrams of salicylic acid or a salicylate salt, 8 milligrams of corn starch binder, 1 milligram of magnesium stearate lubricant, and an enteric coat of keratin.

A dosage form comprising a wax matrix is made by melting carnauba wax to approximately 90° C., to which is added in small portions with constant stirring a mixture, that passes through a 40 mesh screen of 600 milligrams of potassium chloride and 40 milligrams of salicylic acid or a salicylate salt. Then, the matrix is cooled in a tablet shaped mold. The drug after physically incorporated into a wax matrix and molded can be compressed for providing a prolonged sustained release system. Dosage forms comprising a wax matrix of castor wax and the drugs, or carnauba wax and stearyl alcohol and the drugs, beeswax, bayberry wax, and the like are prepared in a similar manner.

A dosage formulation comprising a polymeric coating is fabricated by first blending 450 milligrams of potassium chloride and 30 milligrams of salicylic acid or a salicylate salt, and then compressing the composition under a pressure of 3000 kilograms. The compressed drugs are transferred to a larger die cavity and surrounded with about 250 milligrams of a polymeric coating composition comprising vinyl chloride-vinyl acetate copolymer of particle size 60 to 80 microns average and containing a small amount of lubricant magnesium lauryl sulphate. A pressure of about 3000 kilograms is applied for surrounding the drugs with the polymeric coat. Additional polymers that can be used for forming the polymeric porous coat according to the example include vinylidene chloride-acrylonitrile copolymer, vinylidene chloride-vinyl acetate copolymer, and the like.

As osmotic device is prepared comprising a semipermeable wall of cellulose acetate having an acetyl content of 32% surrounding a compartment containing 750 milligrams of potassium chloride, 50 milligrams of salicylic acid or a salicylate salt and 0.5 milligrams of magnesium stearate. The osmotic device has a wall thickness of 5 mil, a passageway through the wall of 10 mil, a 7/16 inch concave shape, and a release rate of 60 milligrams an hour of potassium chloride and 4 milligrams an hour of salicylic acid or a salicylic salt.

A series of experiments were performed for ascertaining the benefits of the invention. The experiments were performed as follows: a group of conventional, laboratory rabbits were anesthetized and a section of their large intestine separated from the remainder of the intestine by thermocoutery and ligation with the vascular supply to the segment left intact. The section was opened along the antimesenteric border and placed in a grid separated into segments. The segments were used for the purpose of the test, and they were perfused with Ringer's solution at 38° C. After a one hour control period, the drugs to be tested were administered individually, or they were coadministered onto the segments and left there for 4 to 6 hours. Pictures were taken before and after treatment and gross pathology was noted for ascertaining the affect of the drugs on mucosal tissue. The experiment administered sodium salicylate, potassium salicylate, salicylic acid, and potassium chloride alone, and it coadministered sodium salicylate and potassium salicylate, sodium salicylate and potassium chloride, potassium salicylate and potassium chloride, sodium chloride and potassium chloride, distilled water and potassium chloride, and salicylic acid and potassium chloride.

The results of the experiments indicated both sodium salicylate and potassium salicylate produced mucosal ulceration when delivered continually for 5 hours over a dose range of 36 to 360 milligrams an hour. Potassium chloride delivered at the rate of 60 milligrams an hour produced mucosal ulceration when in contact with the rabbit intestinal tissue for 5 hours. The combined delivery of sodium salicylate at a rate of 4 milligrams per hour and potassium chloride at the rate of 60 milligrams per hour did not produce any visible tissue damage or mucosal ulceration and normal peristalsis continued throughout the 5 hour experimental period. The combined delivery of potassium salicylate at a rate of 4 milligram per hour and potassium chloride at the rate of 60 milligrams per hour greatly reduced the ulceration normally seen with delivery of potassium chloride alone. The combined delivery of salicylic acid at a rate of 0.4 to 4.0 milligrams per hour and potassium chloride at the rate of 60 milligrams per hour did not produce visible tissue damage or mucosal ulceration, and normal peristalsis continued throughout the five hour experiment. The co-delivery of sodium chloride at 4 milligrams per hour with 60 milligrams per hour of potassium chloride did not prevent or lessen potassium chloride induced mucosal damage. The co-delivery of sodium salicylate at the rate of 4 milligrams per hour and potassium salicylate at the rate of 41 milligrams evidenced visible mucosal ulceration. The delivery of either sodium salicylate or potassium salicylate alone at the rate of 4 milligrams per hour did not produce any tissue change.

Having now fully described the invention it will be apparent to one of ordinary skill in the art that many changes and modifications can be made without departing from the spirit and the scope of the invention set forth herein.

We claim:

1. A method for treating potassium depletion in an animal in need of potassium replacement, which method comprises administering orally to the animal from 15 milligrams to 1200 milligrams of potassium chloride and an effective amount of a member selected from the group consisting essentially of salicyclic acid and its pharmaceutically acceptable salicylate salts for lessening the incidence of unwanted side effects associated with the therapeutic use of potassium chloride.

2. The method for treating potassium depletion according to claim 1 wherein the animal is a human, the potassium chloride is administered as potassium replacement therapy for reversing the potassium depletion in the human, and the salicylate salt administered therewith is sodium salicylate.

3. The method for treating potassium depletion according to claim 1 wherein the animal is a human, the potassium chloride is administered as potassium replacement therapy for reversing potassium depletion in the human, and the salicylate salt administered is potassium salicylate.

4. The method for treating potassium depletion according to claim 1 wherein the animal is a human, the potassium chloride is administered as potassium replacement therapy for reversing potassium depletion in the human, and the member selected from the group consisting of salicylic acid and its pharmaceutically acceptable salts is administered simultaneously with the potassium chloride.

5. The method for treating potassium depletion according to claim 1 wherein the potassium chloride is administered as replacement for potassium depletion arising from diuretic therapy.

6. A combination diet and therapeutic program for maintaining the potassium requirement of a mammal having a need for potassium, which program comprises feeding the mammal foods high in potassium, and administering to the mammal a composition comprising from 15 milligrams to 1200 milligrams of potassium chloride, and a member from the group consisting of salicylic acid and the pharmaceutically acceptable salts of salicylic acid in an effective amount for lessening the incidence of side effects associated with the use of potassium chloride, thereby maintaining the potassium requirements of the mammal.

7. A method for reversing a potassium deficit in a mammal induced by potassium losses from the gastrointestinal tract and the genitourinary system of the mammal, the improvement comprising administering to the mammal a composition comprising 15 milligrams to 1200 milligrams of potassium chloride and a member selected from the group consisting of salicylic acid and its pharmaceutically acceptable salts in an effective amount for lessening the incidence of unwanted side effects associated with the use of potassium chloride therapy.

8. A method for managing the potassium requirement of an animal in need of exogenous potassium, which method comprises administering orally to the animal a dosage formulation comprising 15 milligrams to 1200 milligrams of potassium chloride and an effective amount of a member selected from the group consisting of salicylic acid and its pharmaceutically acceptable salicylate salts for reducing unwanted side effects arising from potassium chloride therapy.

9. A pharmaceutical composition comprising a therapeutically effective amount of potassium chloride for potassium therapy, and about 0.5 milligrams to 5 milligrams of a member selected from the group consisting of salicylic acid and its pharmaceutically acceptable salicylate salts for each 5 milligrams to 20 milligrams of potassium chloride for lessening the unwanted effect arising from the potassium therapy.

10. The pharmaceutical compositions according to claim 9 wherein the composition is dispersed in a pharmaceutically acceptable polymer.

11. The pharmaceutical composition according to claim 9 wherein the composition is dispersed in a wax matrix.

12. The pharmaceutical composition according to claim 9 wherein the composition is in a drug delivery device.

13. The pharmaceutical composition according to claim 9 wherein the composition is a tablet.

14. A pharmaceutical composition for potassium replacement therapy, wherein the composition comprises from 15 milligrams to 1200 milligrams of potassium chloride, and an effective amount of a member selected from the group consisting essentially of salicylic acid and its pharmaceutically acceptable salicylate salts for lessening the unwanted side effects from said potassium replacement therapy.

15. The pharmaceutical composition according to claim 9 wherein the composition comprises 0.5 milligrams to 5 milligrams of the salicylic salt, sodium salicylate, for each 15 milligrams of potassium chloride.

16. The pharmaceutical composition according to claim 14 wherein the composition comprises 1 milligram to 8 milligrams of the member selected from the group consisting essentially of salicylic acid and its pharmaceutically acceptable salicylate salts.

17. The pharmaceutical composition according to claim 9 wherein the composition comprises 0.5 milligrams to 5 milligrams of the salicylate salt, potassium salicylate, for each 15 milligrams of potassium chloride.

18. The pharmaceutical composition according to claim 9 wherein the composition comprises 0.5 milligrams to 5 milligrams of salicylic acid for each 15 milligrams of potassium chloride.

19. A method according to claim 1 wherein about 0.5 milligram to 5 milligrams of said salicylic acid or salicylate member is administered to the animal.

* * * * *